United States Patent [19]

Ishiguri et al.

[11] Patent Number: 4,473,561
[45] Date of Patent: Sep. 25, 1984

[54] FUNGICIDAL COMPOSITION COMPRISING ALPHA-SUBSTITUTED ETHYLPHOSPHINIC ACIDS OR THEIR SALTS

[75] Inventors: Yukio Ishiguri, Hyogo; Yoshimi Yamada, Kyoto; Toshiro Kato, Hyogo; Mitsuru Sasaki, Osaka; Kunio Mukai, Hyogo, all of Japan

[73] Assignee: Sumitomo Chemical Company, Limited, Osaka, Japan

[21] Appl. No.: 365,957

[22] Filed: Apr. 6, 1982

[30] Foreign Application Priority Data

Apr. 17, 1981 [JP] Japan ............................. 56-58965
Apr. 17, 1981 [JP] Japan ............................. 56-58966

[51] Int. Cl.³ .......................... N01N 9/36; A01N 9/36
[52] U.S. Cl. ........................................ 424/211; 424/217
[58] Field of Search ............................. 424/211, 217

[56] References Cited

U.S. PATENT DOCUMENTS 3,280,131 10/1966 Wakeman et al. ............... 546/151
4,147,780 4/1979 Dingwall et al. ............... 424/211

FOREIGN PATENT DOCUMENTS 0038778 4/1981 European Pat. Off. ........... 546/151

OTHER PUBLICATIONS

Annales de Chimie et de Physique, 23, pp. 289–362, 1891, M. J. Ville.
Arch. Pharm., (Weinhein. Ger.) 302 (7), 554–560, 1969, N. Krentz Kamp et al.
Chem. Abstracts, vol. 51, col. 5349g, 1957 & Chem. Abstracts, Sixth Collective Index, vols. 51–55, Formulas A–C12, p. 83F, 1957–1961.
Chem. Abstracts, vol. 83, No. 189317m, p. 127, Dec. 1975 & JP-A-75 101 536, *Abstract*.

*Primary Examiner*—Sam Rosen
*Assistant Examiner*—John Rollins
*Attorney, Agent, or Firm*—Birch, Stewart, Kolasch & Birch

[57] ABSTRACT

A fungicidal composition which comprises as an active ingredient a fungicidally effective amount of a compound of the formula:

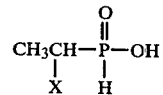

wherein X is a hydroxyl group or a hydroxyamino group, or its salt and an inert carrier or diluent.

19 Claims, No Drawings

FUNGICIDAL COMPOSITION COMPRISING ALPHA-SUBSTITUTED ETHYLPHOSPHINIC ACIDS OR THEIR SALTS

The present invention relates to a fungicidal composition which comprises a fungicidally effective amount of at least one of α-substituted ethylphosphinic acids and their salts as an active ingredient.

The α-substituted ethylphosphinic acids are representable by the formula:

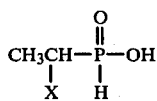

$$\begin{array}{c} \text{O} \\ \parallel \\ \text{CH}_3\text{CH}-\text{P}-\text{OH} \\ | \quad | \\ \text{X} \quad \text{H} \end{array} \quad \text{(I)}$$

wherein X is a hydroxyl group or a hydroxyamino group and cover two compounds, i.e., α-hydroxyethylphosphinic acid (I: X=OH) (Ia) and α-hydroxyaminoethylphosphinic acid (I: X=NHOH) (Ib), which are known and disclosed respectively in Annales de Chimie et de Physique, 23, 289–362 (1891) and Arch. Pharm. (Weinhein. Ger.) 302, (7), 554–560 (1969).

Various fungicides having only a preventive effect have been used for control of plant diseases, such as late blight and downy mildew, which are caused by infection of Phytomycetes. However, their practical use was limited, since a sufficient controlling effect was hardly produced after the invasion of pathogenic fungi into plant bodies.

It has now been found that the α-substituted ethylphosphinic acids (I) and their salts (e.g., acid addition salts, metal salts, quaternary ammonium salts) exhibit not only a preventive effect but also a curative effect against plant diseases such as late blight and downy mildew caused by infection of Phycomycetes. Thus, they are useful as fungicides.

Examples of phytopathogenic fungi belonging to Phycomycetes, against which the α-substituted ethylphosphinic acids (I) and their salts can exert their fungicidal activity, are as follows: *Peronospora brassicae* on vegetables and radish, *Peronospora spinaciae* on spinach, *Peronospora tabacina* on tobacco, *Pseudoperonospora cubensis* on cucumber, *Plasmapara viticola* on grape, *Plasmapara nivea* on Umbelliferae plants, *Phytophthora cactorum* on apple, strawberry and carrot, *Phytophthora capsici* on tomato and cucumber, *Phytophthora cinnamomi* on pineapple, *Phytophthora infestans* on potato, tomato and eggplant, *Phytophthora nicotianae* var. *nicotianae* on tobacco, kidney bean and onion, *Pythium aphanidermatum* on cucumber, Pythium sp. on spinach, Pythium sp. on wheat, *Pythium debaryanum* on tobacco, Pythium rot (i.e., *P. aphanidermatum, P. debaryanum, P. irregulare, P. myriotylum, P. ultimum*) on soybean and so forth.

α-Hydroxyethylphosphinic acid (Ia) is an acidic substance and can be prepared by reacting paraldehyde or acetaldehyde with hypophosphorous acid. When it is reacted with an organic or inorganic base in an inert solvent such as water, an alcohol (e.g., methanol, ethanol), an ether (e.g., tetrahydrofuran, dioxane) or a halogenated hydrocarbon (e.g., chloroform, dichloromethane), its salt is prepared. This salt may be further subjected to salt-exchange with any metal salt in an inert solvent such as water or an alcohol (e.g., methanol, ethanol) to give any other salt. Alternatively, α-hydroxyethylphosphinic acid (Ia) may be treated with a cation exchange resin previously exchanged with an organic amine residue or a metal ion to give the corresponding salt.

Examples of the organic base are alkylamines (e.g., methylamine, ethylamine, n-propylamine, isopropylamine, n-butylamine, isobutylamine, sec-butylamine, tert-butylamine, n-amylamine, isoamylamine, n-hexylamine, cyclo-hexylamine, 2-methylpentylamine), alkenylamines (e.g., allylamine), aralkylamines (e.g., benzylamine, α-phenethylamine, β-phenethylamine, α-naphthylethylamine, α,α-dimethylbenzylamine, p-tolylphenylethylamine), heterocyclic ring-substituted alkylamines (e.g., 2-(2-thienyl)ethylamine, 2-(2-furyl)ethylamine, furfurylamine, 2-thienylmethylamine), dialkylamines (e.g., dimethylamine, diethylamine, methylethylamine, di-n-propylamine, diisopropylamine, di-n-butylamine, diisobutylamine), dialkenylamines (e.g., diallylamine), alkyl-aralkylamines (e.g., methyl-benzylamine, methyl-phenethylamine), trialkylamines (e.g., triethylamine, trimethylamine, tri-n-propylamine, tri-n-butylamine, dimethyl-cyclohexylamine), cyclic amines (e.g., pyrrolidine, piperidine, morpholine, 2-methylpiperidine, 2,6-dimethylmorpholine, piperazine, 4-methylpiperazine, triethylenediamine), alcohol amines (e.g., ethanolamine, N-methylethanolamine, N-isopropylethanolamine, N,N-dimethylethanolamine, diethanolamine, triethanolamine, tris(hydroxymethyl)aminomethane, diglycolamine), alkylenediamines (e.g., ethylenediamine, trimethylenediamine, N,N-dimethylethylenediamine, N,N'-dimethylethylenediamine, N,N,N',N'-tetramethylethylenediamine, N,N-dimethyltrimethylenediamine, N,N,N',N'-tetramethyltrimethylenediamine, 1,2-diaminocyclohexane, N,N-dimethyl-1,2-diaminocyclohexane), hydrazines (e.g., N-methylhydrazine, N,N-dimethylhydrazine, N-phenylhydrazine, N-3-acetylphenylhydrazine), anilines (e.g., aniline, N-methylaniline, diphenylamine, 4-fluoroaniline, 4-chloroaniline, 4-bromoaniline, 4-iodoaniline, 2,4-dichloroaniline, 2,5-dichloroaniline, 3,5-dichloroaniline, 2,4,6-trichloroaniline, 3-trifluoromethylaniline, 4-nitroaniline, 2-methyl-4-methoxyaniline, 3-fluoroaniline, 3-chloroaniline, 3-bromoaniline, 3-iodoaniline, 2,6-dimethylaniline, 2,6-diethylaniline, 4-methylaniline, 4-tert-butylaniline), nitrogen-containing heterocyclic bases (e.g., pyridine, α-picoline, β-picoline, γ-picoline, 2,6-lutidine, collidine, 2-amino-3-methylpyridine, 2,2'-bipyridyl, 4,4'-bipyridyl, 2,4'-bipyridyl, pyrazole, triazole, imidazole, triazine, pirazine, pyrimidine, thiazole, oxazole, isoxazole, quinoline, isoquinoline, pyrrole), etc. Examples of the inorganic base are alkali metal hydroxides (e.g., lithium hydroxide, sodium hydroxide, potassium hydroxide), ammonia, hydrazine, etc.

Examples of the metal salt are carbonates (e.g., calcium(II) carbonate, barium(II) carbonate, thallium(I) carbonate), acetates (e.g., zinc(II) acetate, calcium(II) acetate, barium(II) acetate, magnesium(II) acetate, manganese(II) acetate, nickel(II) acetate, cobalt(II) acetate, copper(II) acetate), nitrates (e.g., calcium(II) nitrate, barium(II) nitrate, magnesium(II) nitrate, aluminum(III) nitrate, manganese(II) nitrate, iron(III) nitrate, zinc(II) nitrate, nickel(II) nitrate, copper(II) nitrate, cobalt(II) nitrate), chlorides (e.g., calcium(II) chloride, barium(II) chloride, magnesium(II) chloride, iron(II) chloride, iron(III) chloride, zinc(II) chloride, tin(II) chloride, tin(IV) chloride, nickel(II) chloride, copper(II) chloride, cobalt(II) chloride, titanium(IV) chloride), lactates (e.g., aluminum(III) lactate), etc.

For purification of α-hydroxyethylphosphinic acid (Ia), the reaction product from the reaction between paraldehyde or acetaldehyde and hypophosphorous acid is, for instance, treated with t-butylamine or α-naphthylethylamine, the produced salt is purified by fractional recrystallization or the like and then the purified salt is treated with an ion exchange resin.

α-Hydroxyaminoethylphosphinic acid (Ib) is an amphoteric substance and can be prepared by reacting acetaldoxime with hypophosphorous acid. When it is reacted with a strong organic or inorganic acid or base in the presence or absence of an inert solvent such as water or an alcohol (e.g., methanol, ethanol), its salt is prepared. Examples of the strong organic or inorganic acid are hydrochloric acid, sulfuric acid, trifluoroacetic acid, p-toluenesulfonic acid, trifluoromethanesulfonic acid, etc. Examples of the strong organic or inorganic base are lithium hydroxide, sodium hydroxide, potassium hydroxide, tetramethylammonium hydroxide, tetra-n-butylammonium hydroxide, etc. Such or any other salt is also obtainable by the use of an ion exchange resin.

For purification of α-hydroxyaminoethylphosphinic acid (Ib), the reaction product from the reaction between acetaldoxime and hypophosphorous acid is, for instance, treated with a cation exchange resin.

Some typical examples of the preparation of the α-substituted ethylphosphinic acid (I) or its salt are shown in the following examples:

EXAMPLE 1

Preparation of α-hydroxyethylphosphinic acid and tert-butylammonium α-hydroxyethylphosphinate:

Hydrophosphorous acid (263 g) obtained by concentrating a 50% aqueous solution of hypophosphorous acid (488 g; 3.7 mol) at a bath temperature of not higher than 50° C. under reduced pressure was dissolved in tetrahydrofuran (370 g), paraldehyde (22 g; 1.67 mol) was added thereto, and the resultant mixture was stirred at room temperature for 5 days. Removal of tetrahydrofuran from the reaction mixture by distillation affords crude α-hydroxyethylphosphinic acid (433.3 g). By measurement of $^{31}$P-NMR, this substance was confirmed to contain less than 15% by weight of bis-(α-hydroxyethylphosphinic acid) in addition to α-hydroxyethylphosphinic acid.

The above obtained crude α-hydroxyethylphosphinic acid (433.3 g) was dissolved in methanol (1000 ml), and tert-butylamine (288 g; 3.9 mol) was added thereto at a temperature of not higher than 50° C. while cooling with ice. The resultant mixture was allowed to stand overnight, and methanol was distilled off. To the residue, methanol (400 ml) and acetonitrile (800 ml) were added, and the resultant mixture was refluxed. After cooling, the precipitated crystals were collected by filtration to give tert-butylammonium α-hydroxyethylphosphinate (Compound No. 16) (388 g). M.P., 153° C. Yield, 57.3%.

The above obtained tert-butylammonium α-hydroxyethylphosphinate (251 g; 1.37 mol) was dissolved in distilled water (1500 ml), a cation exchange resin (Dowex 50W ×4H+ type; 2500 g) was added thereto, and stirring was continued at room temperature for 1 hour. After filtration, the filtrate was concentrated to give pure α-hydroxyethylphosphinic acid (Compound No. 1) (140.3 g). $n_D^{23.0}$ 1.4780. Yield, 93.1%. No peak due to any impurity was recognized in NMR.

EXAMPLE 2

Preparation of α-hydroxyethylphosphinic acid and α-naphthylethylammonium α-hydroxyethylphosphinate:

Crude α-hydroxyethylphosphinic acid (57.7 g; 0.524 mol) prepared as in Example 1 was dissolved in methanol (290 ml). α-Naphthylethylamine (90.2 g; 0.575 mol) was added thereto at a temperature of not more than 50° C. while stirring. The reaction mixture was kept at a temperature of 25° to 30° C. for 30 minutes, followed by distillation of methanol to give a foamy substance. To the foamy substance, methanol (60 ml) and acetonitrile (600 ml) were added, followed by vigorous stirring, whereby crystals were precipitated. To the resultant mixture, methanol (130 ml) was added, followed by heating with reflux. After cooling, precipitated crystals were collected by filtration to give (±)-α-naphthylethylammonium α-hydroxyethylphosphinate (Compound No. 22) (56.0 g). M.P., 164° C. Yield, 37.8%. The mother liquor was concentrated, and the residue was recrystallized from a mixture of acetonitrile (400 ml) and methanol (105 ml) to give (±)-α-naphthylethylammonium α-hydroxyethylphosphinate (23.0 g). The thus prepared (±)-α-naphthylethylammonium α-hydroxyethylphosphinate (73.6 g; 0.2616 mol) was dissolved in distilled water (500 ml), cation exchange resin (Dowex 50W ×8H+ type; 600 g) was added thereto, and the resultant mixture was stirred for 40 minutes. After separation of the resin, the filtrate was concentrated to give pure α-hydroxyethylphosphinic acid (Compound No. 1) (27.0 g). Yield, 93.8%. No peak due to any impurity was recognized by NMR.

EXAMPLE 3

Preparation of α-hydroxyethylaminophosphinic acid:

Under nitrogen, acetaldoxime (3.54 g; 0.06 mol) and hypophosphorous acid (1.32 g; 0.02 mol) were mixed together at room temperature, and the resultant mixture was stirred at such temperature for 2 hours and at 50° C. for 1 hour. After cooling, the reaction mixture was added to water (5 g) and washed five times with methylene chloride (each 5 ml). To the water layer, cation exchange resin (Dowex 50W ×8H+ type; 20 g) and water (10 ml) were added, followed by stirring for 1 hour. The resin was collected by filtration, washed two times with water (each 10 ml) and stirred with 10% ammonia water (50 ml) for 1 hour. The resin was filtered, and the filtrate was concentrated to give α-hydroxyethylaminophosphinic acid (Compound No. 24) (0.7 g). M.P., 95°–100° C. (decomposition with foaming).

EXAMPLE 4

Preparation of sodium α-hydroxyethylphosphinate:

To a solution of α-hydroxyethylphosphinic acid (330 mg) in water (2 ml), a solution of sodium hydroxide (120 mg) in water (1 ml) was added, followed by stirring for 1 hour. The reaction mixture was concentrated under highly reduced pressure to give sodium α-hydroxyethylphosphinate (Compound No. 3) (360 mg) as a hygroscopic solid.

EXAMPLE 5

Preparation of aluminum α-hydroxyethylphosphinate:

To a solution of aluminum lactate (50 g) in distilled water (1800 ml), weakly acidic cation exchange resin (Dowex CCR-2 H+ type; 250 g) was added, and the resulting mixture was stirred for 1 hour. The resultant mixture was allowed to stand, and the supernatant was eliminated. To the residue, distilled water (500 ml) was added, and the resulting mixture was stirred for 30 minutes and then filtered. The resin was washed with distilled water and added to a solution of α-hydroxyethylphosphinic acid (17 g) in water (150 ml), followed by stirring for 1 hour. The resulting mixture was filtered, and the collected resin was washed with distilled water. The filtrate was concentrated to give aluminum α-hydroxyethylphosphinate (Compound No. 5) (17.0 g) as a hygroscopic solid.

EXAMPLE 6

Preparation of copper(II) α-hydroxyethylphosphinate:

To a solution of α-hydroxyethylphosphinic acid (18 g) in distilled water (30 ml) previously adjusted to pH 8 with an aqueous solution of sodium hydroxide, a solution of copper(II) (10.7 g) in distilled water (70 ml) was added, followed by stirring for 30 minutes. After elimination of water by distillation, anhydrous ethanol (300 ml) was added thereto, and stirring was continued for 30 minutes. The by-produced sodium chloride was separated by filtration. The filtrate was concentrated to give copper(II) α-hydroxyethylphosphinate (Compound No. 11) (21.45 g) as pale green crystals. M.P. ~105° C. (decomp.).

EXAMPLE 7

Preparation of morpholinium α-hydroxyethylphosphinate:

To a solution of α-hydroxyethylphosphinic acid (330 mg) in methanol, a solution of morpholine (261 mg) in methanol (1 ml) was added, and the resultant mixture was stirred for 2 hours. After removal of methanol by distillation, there was obtained morpholinium α-hydroxyethylphosphinate (Compound No. 14) (556 mg). $n_D^{24.5}$ 1.4621.

Some examples of the α-substituted ethylphosphinic acids (I) and their salts prepared as above are shown in Table 1:

TABLE 1

$$\left( CH_3CH\underset{X}{\underset{|}{-}}\underset{H}{\underset{|}{P}}\overset{O}{\overset{\|}{-}}O^- \right)_n Y^{n+}$$

| Compound No. | X | Y | n | Physical property |
|---|---|---|---|---|
| 1 | OH | H | 1 | $n_D^{23}$ 1.4780 |
| 2 | OH | Li | 1 | hygroscopic solid |
| 3 | OH | Na | 1 | hygroscopic solid |
| 4 | OH | K | 1 | hygroscopic solid |
| 5 | OH | Al | 3 | M.P. 144° C. (decomp.) |
| 6 | OH | Ca | 2 | M.P. 150° C. (decomp.) |
| 7 | OH | Ba | 2 | M.P. ~115° C. (decomp.) |
| 8 | OH | Mg | 2 | M.P. ~120° C. (decomp.) |
| 9 | OH | Mn | 2 | M.P. ~140° C. (decomp.) |
| 10 | OH | Fe | 3 | M.P. 205° C. (decomp.) |
| 11 | OH | Cu | 2 | M.P. ~105° C. (decomp.) |

TABLE 1-continued $$\left( CH_3CH\underset{X}{\underset{|}{-}}\underset{H}{\underset{|}{P}}\overset{O}{\overset{\|}{-}}O^- \right)_n Y^{n+}$$

| Compound No. | X | Y | n | Physical property |
|---|---|---|---|---|
| 12 | OH | Ni | 2 | M.P. ~150° C. (decomp.) |
| 13 | OH | NH₄ | 1 | $n_D^{22.5}$ 1.4840 |
| 14 | OH | morpholinium (H₂N⌒O) | 1 | $n_D^{24.5}$ 1.4621 |
| 15 | OH | iso-C₃H₇NH₃ | 1 | $n_D^{24.0}$ 1.4700 |
| 16 | OH | tert-C₄H₉NH₃ | 1 | M.P. 153° C. |
| 17 | OH | C₆H₅C(CH₃)₂NH₃ | 1 | $n_D^{22.0}$ 1.5345 |
| 18 | OH | HOCH₂CH₂NH₃ | 1 | $n_D^{23.8}$ 1.4843 |
| 19 | OH | (C₂H₅)₃NH | 1 | $n_D^{23.6}$ 1.4736 |
| 20 | OH | C₆H₁₁—NH₃ | 1 | M.P. 112–118° C. |
| 21 | OH | NH₃NH₂ | 1 | $n_D^{22.5}$ 1.5052 |
| 22 | OH | naphthyl-CH(CH₃)—NH₃ | 1 | M.P. 164° C. |
| 23 | OH | C₆H₅—NH₃ | 1 | $n_D^{22.6}$ 1.5411 |
| 24 | NHOH | H | 1 | M.P. 95–100° C. |
| 25 | NHOH | Na | 1 | resinous material |
| 26 | NHOH | Al | 3 | resinous material |

In actual application as fungicides, the α-substituted ethylphosphinic acids (I) and their salts may be used alone without incorporation of other ingredients such as carriers and diluents or, for easier application, in admixture with solid or liquid carriers. The fungicidal compositions can be formulated into any of ordinarily adopted forms such as, for example, dusts, granules, wettable powders, emulsifiable concentrates, fine particles, aqueous solutions, oil sprays, aerosols and tablets.

The foregoing compositions generally contain 0.1 to 99.9% by weight, preferably 2.0 to 80.0% by weight of the active ingredient.

As the solid carriers or diluents to give used for formulation of the fungicidal composition of this invention, there may be used plant carriers (e.g., wheat flour, tobacco powder, soybean powder, walnut-shell powder, wooden powder, saw dust, wheat bran, bark dust, cellulose powder, extract residue), fibrous products (e.g., paper, card board, rag), crushed synthetic resins, clays (e.g., kaoline, bentonite, terra alba), talcs, other inorganic minerals (e.g., pyrophyllite, celicite, pumice, sulfur powder, diatomaceous earth, white carbon, activated carbon), chemical fertilizers (e.g., ammonium sulfate, ammonium phosphate, ammonium nitrate, urea, ammonium chloride), etc. As the liquid carriers or diluents, there may be employed water, alcohols (e.g., methanol, ethanol), ketones (e.g., acetone, methylethylketone), ethers (e.g., diethyl ether, dioxane, cellosolve, tetrahydrofuran), aromatic hydrocarbons (e.g., benzene, toluene, xylene, methylnaphthalene), aliphatic hydrocarbons (e.g., gasoline, kerosene, lamp oil), esters, nitriles, acid amides (e.g., methylformamide, dimethylacetamide), halogenated hydrocarbons (e.g., dichloroethane, trichloroethylene, carbon tetrachloride), etc.

In addition to the solid or liquid carriers or diluents as exemplified above, there may be used surfactants when desired. Examples of the surfactants are polyoxyethylene phenylphenol polymer, polyoxyethylene alkylaryl ether, sodium laurylsulfate, calcium alkylbenzenesulfonate, alkylsulfates, alkylsulfonates, alkylarylsulfonates, polyethyleneglycol ethers, polyvalent alcohol esters, etc. There may be also used adhesive agents, dispersing agents, stabilizers, etc. Their specific examples are casein, gelatin, starch, carboxymethyl cellulose, gum arabic, alginate, calcium ligninsulfonate, bentonite, molasse, polyvinyl alcohol, palm tree oil, agar, isopropyl phosphate, tricresyl phosphate, tall oil, epoxylated oil, surfactants, aliphatic acids and their esters, etc.

Moreover, the fungicidal composition may comprise other fungicides, insecticides, nematocides, acaricides, insect repellents, plant growth regulators, herbicies, fertilizers, soil improvers, etc.

Some typical examples of the fungicidal composition according to this invention are shown below. In those examples, part(s) and % are by weight unless otherwise indicated.

EXAMPLE A

Compound No. 15 (2 parts), clay (88 parts) and talc (10 parts) were thoroughly pulverized and mixed together to obtain a dust containing 2% of the active ingredient.

EXAMPLE B

Compound No. 26 (30 parts), diatomaceous earth (45 parts), white carbon (20 parts), a wetting agent (sodium laurylsulfate) (3 parts) and a dispersing agent (calcium ligninsulfonate) (2 parts) were thoroughly pulveried and mixed together to obtain a wettable powder containing 30% of the active ingredient.

EXAMPLE C

Compound No. 16 (50 parts), diatomaceous earth (45 parts), a wetting agent (calcium alkylbenzenesulfonate) (2.5 parts) and a dispersing agent (calcium ligninsulfonate) (2.5 parts) were thoroughly pulverized and mixed togethe to obtain a wettable powder containing 50% of the active ingredient.

EXAMPLE D

Compound No. 1 (20 parts), xylene (60 parts) and an emulsifier (polyoxyethylene phenylphenol polymer type) (20 parts) were mixed together to obtain an emulsifiable concentrate containing 20% of the active ingredient.

EXAMPLE E

Compound No. 24 (50 parts), water (45 parts) and a wetting agent (polyoxyethylene alkylaryl ether type) (5 parts) were mixed together to obtain an aqueous solution containing 50% of the active ingredient.

A suitable amount of the fungicidal composition of the invention to be applied is generally from 50 to 5000 grams in terms of the active ingredient per 10 are. In case of the composition form such as wettable powder, emulsifiable concentrate or aqueous solution, it is normally diluted with water and then applied. The concentration of the active ingredient on the application is preferably within the range of 0.005 to 0.5%. In case of the composition form such as dust or granule, it is ordinarily applied as such. Since, however, the amount and concentration largely depend upon the composition forms, application times, application methods, application sites, diseases and crops, they may be properly increased or decreased appropriately.

The following examples show some typical test data supporting the excellent fungicidal activity of the α-substituted ethylphosphinic acids (I) and their salts. In these examples, the compound numbers correspond to those in Table 1. The compounds used for comparison are as follows:

| Compound No. | Structure | Remarks |
|---|---|---|
| A | $HOCH_2-P(=O)(H)(OH)$ | Prepared for comparison |
| B | $CH_3CH_2CH(OH)-P(=O)(H)(OH)$ | Prepared for comparison |
| C | $CH_3CH_2CH_2CH(OH)-P(=O)(H)(OH)$ | Prepared for comparison |
| D | $CH_3CH(NH_2)-P(=O)(H)(OH)$ | U.S. Pat. No. 4,147,780 |
| E | $[(CH_3CH_2O)(H)P(=O)(O^-)]_3 Al^{3+}$ | Commercially available fungicide "Alliete" |
| F | tetrachloroisophthalonitrile (Cl$_4$C$_6$(CN)$_2$) | Comercially available fungicide "Daconil" |
| G | $[CH_2(NH-CS-S^-)]_2 Zn^{2+}$ | Commercially available fungicide "Zineb" |
| H | $[CH_2(NH-CS-S^-)]_2 Mn^{2+}$ | Commerically available fungicide "Maneb" |

EXAMPLE I

Seeds of cucumber (species: "Sagamihanjiro") were sowed in soil filled in plastic pots and cultivated in a greenhouse for 14 days to obtain seedlings of cucumber having cotyledons. An aqueous dilution of the test compound in the form of emulsifiable concentrate or wettable powder was applied onto the seedlings by foliar treatment. Then, the seedlings were grown in the greenhouse for 5 days. A spore suspension of *Pseudoperonospora cubensis* was sprayed onto the seedlings, which were placed at 20° C. under a humid condition for 3 days and then grown at 20° C. under the irradiation with a fluorescent lamp for 3 days. The state of infection of the plants was observed, and the preventive value was calculated according to the following equations:

| Infection index | State of infection |
|---|---|
| 0 | No infectious spot on leaf |
| 0.5 | Infectious spots of less than 5% of the area of leaf |
| 1 | Infectious spots of less than 20% of the area of leaf |
| 2 | Infectious spots of less than 50% of the area of leaf |
| 4 | Infectious spots of not less than 50% of the area of leaf |

$$\text{Degree of infection (\%)} = \frac{\Sigma(\text{infection index}) \times (\text{Number of leaves})}{(\text{Total number of leaves}) \times 4} \times 100$$

$$\text{Preventive value (\%)} = 100 - \frac{(\text{Degree of infection in medicated plot})}{(\text{Degree of infection in non-medicated plot})} \times 100$$

The results are shown in Table 2.

TABLE 2

| Compound No. | Concentration of active ingredient (ppm) | Preventive value (%) |
|---|---|---|
| 1 | 200 | 100 |
| 2 | 200 | 100 |
| 3 | 200 | 100 |
| 4 | 200 | 100 |
| 5 | 200 | 100 |
| 6 | 200 | 100 |
| 7 | 200 | 100 |
| 8 | 200 | 100 |
| 9 | 200 | 100 |
| 10 | 200 | 100 |
| 11 | 200 | 100 |
| 12 | 200 | 100 |
| 13 | 200 | 100 |
| 14 | 200 | 100 |
| 15 | 200 | 100 |
| 16 | 200 | 100 |
| 17 | 200 | 100 |
| 18 | 200 | 100 |
| 19 | 200 | 100 |
| 20 | 200 | 100 |
| 21 | 200 | 100 |
| 22 | 200 | 100 |
| 23 | 200 | 100 |
| 24 | 200 | 100 |
| 25 | 200 | 100 |
| 26 | 200 | 100 |
| A | 200 | 0 |
| B | 200 | 0 |
| C | 200 | 0 |
| D | 200 | 85 |
| E | 200 | 44 |
| F | 200 | 90 |

EXAMPLE II

Seeds of cucumber (species: "Sagamihanjiro") were sowed in soil filled in plastic pots and cultivated in a greenhouse for 14 days to obtain seedlings of cucumber having cotyledons. The seedlings were treated by soil-drench with an aqueous dilution of the test compound in the form of emulsifiable concentrate or wettable powder. After 4 days, a spore suspension of *Pseudoperonospora cubensis* was sprayed onto the seedlings, which were placed at 20° C. under a humid condition for 3 days and then grown at 20° C. under the irradiation with a fluorescent lamp for 4 days. The state of infection of the plants was observed, and the preventive value was calculated as in Example I.

The results are shown in Table 3.

TABLE 3

| Compound No. | Concentration of active ingredient (ppm) | Preventive value (%) |
|---|---|---|
| 1 | 125 | 100 |
| 3 | 125 | 100 |
| 5 | 125 | 100 |
| 9 | 125 | 100 |
| 10 | 125 | 100 |
| 11 | 125 | 100 |
| 24 | 125 | 100 |
| 26 | 125 | 100 |
| E | 125 | 25 |
| F | 250 | 10 |

EXAMPLE III

Seeds of grape (species: "Delaware") were sowed in soil filled in plastic pots and cultivated in a greenhouse for 1 month to obtain seedlings of grape at the 2 to 3-leaved stage. A spore suspension of *Plasmopara viticola* was sprayed onto the seedlings, which were placed at 23° C. under a humid condition for 3 days. Then, an aqueous dilution of the test compound in the form of emulsifiable concentrate or wettable powder was applied onto the seedlings by foliar treatment. Thereafter, the seedlings were grown at 23° C. under the irradiation with a fluorescent lamp for 14 days. The state of infection of the plants was observed, and the preventive value was calculated as in Example I.

The results are shown in Table 4.

TABLE 4

| Compound No. | Concentration of active ingredient (ppm) | Preventive value (%) |
|---|---|---|
| 1 | 500 | 100 |
| 5 | 500 | 100 |
| 6 | 500 | 100 |
| 11 | 500 | 100 |
| 13 | 500 | 100 |
| 24 | 500 | 100 |
| 25 | 500 | 100 |
| E | 500 | 69 |
| G | 1000 | 15 |

EXAMPLE IV

Seeds of tomato (species: "Ponterosa") were sowed in soil filled in plastic pots and cultivated in a greenhouse for 30 days to obtain seedlings of tomato at the 5 to 6-leaved stage. A spore suspension of Phytophthora infestans was sprayed onto the seedlings, which were placed at 20° C. under a humid condition for 20 hours. Then, an aqueous dilution of the test compound in the form of emulsifiable concentrate or wettable powder was applied onto the seedlings by foliar treatment. Thereafter, the seedlings were grown at 20° C. under a humid condition for 6 days. The state of infection of the plants was observed, and the preventive value was calculated as in Example I.

The results are shown in Table 5.

TABLE 5

| Compound No. | Concentration of active ingredient (ppm) | Preventive value (%) |
|---|---|---|
| 1 | 500 | 96 |
| 3 | 500 | 93 |
| 5 | 500 | 97 |
| 8 | 500 | 91 |
| 11 | 500 | 95 |
| 24 | 500 | 94 |
| 25 | 500 | 91 |
| 26 | 500 | 95 |
| D | 500 | 46 |
| H | 1000 | 5 |

EXAMPLE V

Seeds of potato (species: "Danshaku") were sowed in soil filled in plastic pots and cultivated in a greenhouse for 2 months to obtain seedlings of potato. A spore suspension of *Phytophthora infestans* was sprayed onto the seedlings, which were placed at 20° C. under a humid condition for 20 hours. Then, an aqueous dilution of the test compound in the form of emulsifiable concentrate or wettable powder was applied onto the seedlings by foliar treatment. Thereafter, the seedlings were grown at 20° C. under a humid condition for 6 days. The state of infection of the plants was observed, and the preventive value was calculated as in Example I.

The results are shown in Table 6.

TABLE 6

| Compound No. | Concentration of active ingredient (ppm) | Preventive value (%) |
|---|---|---|
| 1 | 500 | 91 |
| 3 | 500 | 98 |
| 5 | 500 | 90 |
| 8 | 500 | 97 |
| 11 | 500 | 93 |
| 13 | 500 | 99 |
| 24 | 500 | 90 |
| 25 | 500 | 85 |
| 26 | 500 | 91 |
| H | 1000 | 15 |

EXAMPLE VI

Seeds of cucumber (species: "Sagamihanjiro") were sowed in soil filled in plastic pots and cultivated in a greenhouse for 8 days to obtain seedlings of cucumber having cotyledons. A spore suspension of *Phytophthora capcisi* was sprayed onto the seedlings, which were placed at 28° C. under a humid condition for 20 hours. Then, an aqueous dilution of the test compound in the form of emulsifiable concentrate or wettable power was applied onto the seedlings by foliar treatment. Thereafter, the seedlings were grown at 28° C. under a humid condition for 6 days. The state of infection of the plants was observed, and the preventive value was calculated as in Example I.

The results are shown in Table 7.

TABLE 7

| Compound No. | Concentration of active ingredient (ppm) | Preventive value (%) |
|---|---|---|
| 1 | 500 | 100 |
| 3 | 500 | 100 |
| 5 | 500 | 100 |
| 9 | 500 | 100 |
| 11 | 500 | 100 |

TABLE 7-continued

| Compound No. | Concentration of active ingredient (ppm) | Preventive value (%) |
|---|---|---|
| 24 | 500 | 100 |
| 26 | 500 | 100 |
| H | 1000 | 10 |

What is claimed is:

1. A fungicidal composition adapted for application to plant life which comprises as an active ingredient a fungicidally effective and agriculturally acceptable amount of a compound of the formula:

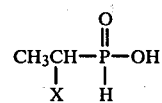

wherein X is a hydroxyl group or a hydroxyamino group, or an organic or inorganic salt thereof and an agriculturally acceptable solid carrier or diluent.

2. The composition according to claim 1, wherein X is a hydroxyl group.

3. The composition according to claim 1, wherein said salt is selected from the group consisting of alkylamines, alkenylamines, aralkylamines, heterocyclic ring-substituted alkylamines, dialkylamines, dialkenylamines, alkylaralkylamines, trialkylamines, cyclic amines, alcohol amines, alkylenediamines, hydrazines, anilines, nitrogen-containing heterocyclic bases, alkali metal hydroxides, ammonia and metals.

4. The composition according to claim 1, wherein said carrier or diluent is selected from the group consisting of fibrous products, crushed synthetic resins, clays, talcs, and chemical fertilizers.

5. The composition according to claim 1, in the form of a dust.

6. The composition according to claim 1, wherein said solid carrier or diluent is clay or talc.

7. The composition according to claim 1, in the form of a wettable powder.

8. The composition according to claim 7, wherein said composition comprises a solid carrier or diluent, a wetting agent and a dispersing agent.

9. A fungicidal composition in the form of an emulsifiable concentrate which comprises as an active ingredient an effective fungicidal amount of a compound of the formula:

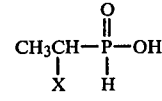

wherein X is a hydroxyl group or a hydroxyamino group, or an organic or inorganic salt thereof; an agriculturally acceptable organic solvent for said compound and emulsifier.

10. An aqueous funicidal composition which comprises as an active ingredient an effective fungicidal and agriculturally acceptable amount of a compound of the formula:

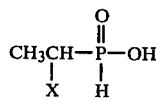

wherein X is a hydroxyl group or a hydroxyamino group, or an organic or inorganic salt thereof, water and a wetting agent.

11. A fungicidal composition which comprises as an active ingredient a fungicidally effective and agriculturally acceptable amount of a compound of the formula:

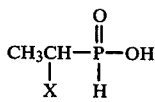

wherein X is a hydroxyl group or a hydroxyamino group or an acid addition, metal or quaternary ammonium salt thereof and an agriculturally acceptable ingredient selected from the group consisting of a solid carrier and a surfactant.

12. The fungicidal composition according to claim 11, which contains a surfactant.

13. An aqueous composition which comprises as an active ingredient 2.0 to 80.0% by weight of a compound of the formula:

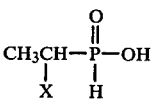

wherein X is a hydroxyl group or a hydroxyamino group or an acid addition, metal or quaternary ammonium salt thereof; a surfactant; and water.

14. A method for preventing fungicidal diseases in plants which comprises applying to plants a fungicidally effective amount of a composition which comprises as an active ingredient a fungicidally effective and agriculturally acceptable amount of a compound of the formula:

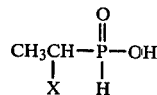

wherein X is a hydroxyl group or a hydroxyamino group, or an organic or inorganic salt thereof and an agriculturally acceptable carrier or diluent.

15. The method of claim 14, wherein the plant diseases are those caused by fungi belonging to Phycomycetes.

16. A method for curing fungicidal diseases in plants which comprises applying to plants a fungicidally effective amount of a composition which comprises as an active ingredient a fungicidally effective and agriculturally acceptable amount of a compound of the formula:

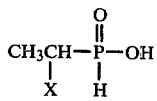

wherein X is a hydroxyl group or a hydroxyamino group, or an organic or inorganic salt thereof and an agriculturally acceptable carrier or diluent.

17. The method of claim 16, wherein the plant diseases are those caused by fungi belonging to Phycomycetes.

18. The method of claim 16, wherein the plant diseases are late blight and downy mildew caused by infection of *Peronopora brassicae* on vegetables and radish, *Peronospora tabacina* on tobacco, *Pseudoperonospora cubensis* on cucumber, *Plasmapara viticola* on grape, *Plasmapara nivea* on Umbelliferae plants, *Phytophthora cactorum* on apple, strawberry and carrot, *Phytophthora capsici* on tomato and cucumber, *Phytophthora cinnamomi* on pineapple, *Phytophthora infestans* on potato, tomato and eggplant, *Phytophthora* var. *nicotianae* on tobacco, kidney bean and onion, *Phythium aphanidermatum* on cucumber, *Pythium* sp. on spinach, *Pythium* sp. on wheat, *Pythium debaryanum* on tobacco or Pythium rot on soybean.

19. The method of claim 16, wherein the composition is applied in an amount of from 50 to 5000 grams in terms of the active ingredient per 10 acres and the concentration of the active ingredient on application is within the range of 0.005 to 0.5%.

* * * * *